United States Patent [19]
Sagner et al.

[11] Patent Number: 6,004,530
[45] Date of Patent: Dec. 21, 1999

[54] USE OF METALLO-PORPHYRIN CONJUGATES FOR THE DETECTION OF BIOLOGICAL SUBSTANCES

[75] Inventors: Gregor Sagner, Penzberg, Germany; Richard Robert De Haas, Heiden, Netherlands; Rob Van Gijlswijk, Rijn, Netherlands; Hans Tanke, Rijnsburg, Netherlands

[73] Assignee: Roche Diagnostics GmbH, Mannheim, Germany

[21] Appl. No.: 08/866,043

[22] Filed: May 30, 1997

[30] Foreign Application Priority Data

Jun. 4, 1996 [EP] European Pat. Off. .............. 96108951

[51] Int. Cl.$^6$ .............................. A61K 51/00; A61B 8/00; C07D 487/22; C09B 47/04
[52] U.S. Cl. ..................... 424/1.65; 424/1.85; 424/9.61; 540/121; 540/122; 540/145
[58] Field of Search .................................. 424/9.61, 1.65, 424/1.85; 540/145, 121, 122

[56] References Cited

U.S. PATENT DOCUMENTS 4,375,972  3/1983  Forgione et al. ........................ 436/531
4,877,872  10/1989 Morgan et al. ......................... 540/145

FOREIGN PATENT DOCUMENTS 0 127 797  5/1984  European Pat. Off. .
9529921  11/1995  WIPO .

OTHER PUBLICATIONS

Yu et al, Analytical Biochemistry, vol. 219, pp. 109–114, (1994) Universal Phosphorescence Immunoassay.

*Primary Examiner*—Mukund J. Shah
*Assistant Examiner*—Tamthom N. Truong
*Attorney, Agent, or Firm*—Nikaido Marmelstein Murray & Oram, LLP

[57] ABSTRACT

The present invention refers to a process for the preparation of an activated metallo-porphyrin derivative and to novel activated metallo-porphyrin derivatives obtainable by said process. Further, the present invention refers to conjugates of metallo-porphyrins with molecules having at least one primary amino group, especially biomolecules. The conjugates are used in a procedure for the detection of a biological substance, especially in an immunoassay or a nucleic acid hybridization assay.

29 Claims, 2 Drawing Sheets

Fig.2

Pt-MESO-TETRA (4-CARBOXYPHENYL) PORPHINE
EXCITATION: 400nm, 514 nm
EMISSION: 670 nm

Fig.1

Pt-
3, 8, 13, 18-TETRAMETHYL-21H, 23H-PORPHINE-
2, 7, 12, 17-TETRAPROPIONIC ACID

EXCITATION: 380 nm, 496 nm, 530 nm
EMISSION: 650 nm

Fig.3

PORPHYRIN - COOH + DCC

+ HOBT

HOSu

USE OF METALLO-PORPHYRIN CONJUGATES FOR THE DETECTION OF BIOLOGICAL SUBSTANCES

SPECIFICATION

The present invention refers to a process for the preparation of an activated metallo-porphyrin derivative and to novel activated metallo-porphyrin derivatives obtainable by said process. Further, the present invention refers to conjugates of metallo-porphyrins with molecules having at least one primary amino group, especially biomolecules. The conjugates are used in a procedure for the detection of a biological substance, especially in an immunoassay or a nucleic acid hybridization assay.

Porphyrins are substituted tetra-pyrrole structures in which pyrroles are coupled together with methylene bridges forming cyclic conjugated structures with chelating inner cavities. They are found in a number of biological and synthetic pigments such as hemin and hemin-proteins (hemoglobin, myoglobin cytochrome) chlorophylls etc.

Porphyrins exhibit strong luminescent properties. Metallo-porphyrins such as Pt- and Pd-metallo-porphyrins are known to exhibit phosphorescence at room temperature in suitable solvents. Several applications for porphyrins and metalloporphyrins are known in the prior art. EP-A-0 071 991 and EP-A-0 127 797 disclose procedures of using porphyrins as labels in fluorescence immunoassays. In EP-A-0 127 797 the porphyrins are coupled to an antibody by contacting a porphyrin derivative having one carboxylic acid group with a water soluble carbodiimide derivative and then contacting the resulting product with the antibody. In EP-A-0071 991 the metallo-porphyrin bacteriochlorophyll b is coupled to various biomolecules via carbodiimide, isobutylchloroformate/dioxane, glutaraldehyde or succinic anhydride/pyridine/carbodiimide.

In a publication by Mantrova et al (Anal. Biochem. 219 (194), 109–114) the use of metallo-porphyrin antibody conjugates in a phosphorescence immunoassay is disclosed. The coupling of the metallo-porphyrin to the antibody is carried out as described in EP-A-0 127 797.

A disadvantage of the metallo-porphyrin conjugates known from the prior art, however, consists in the fact that they are not suited for in situ applications, i.e. the detection of cellular macromolecules in tissue extracts and morphologically intact cells. Also a series of other methods for coupling labelling groups to biomolecules, known from the stated prior art, turned out to be not suited for the production of metallo-porphyrin conjugates, which can be used for in situ applications.

Thus, the problem underlying the present invention was to provide a method for the preparation of metallo-porphyrin conjugates which are suitable for in situ applications.

This problem is solved by a process for the preparation of an activated metallo-porphyrin derivative having the general formula (I):

$$M\,P{-}(RCOOX)_n \qquad (I)$$

wherein M is palladium or platinum,
P is a porphyrin moiety,
RCOOX is an activated carboxylic acid ester group which is covalently bound to the porphyrin moiety,
R is independently in each occurrence a chemical bond, or a linker group, and
n is from 1 to 4, wherein a metallo-porphyrin having the general formula (II):

$$M\,P{-}(RCOOH)_m \qquad (II)$$

wherein M, P and R are defined as above and m is the number of carboxylic acid groups covalently bound to the porphyrin moiety, is reacted with a carbodiimide, 1-hydroxybenzothiazole and an active ester coupling agent in an organic solvent, and the resulting reactive metallo-porphyrin derivative (I) is obtained. surprisingly it was found that a metallo-porphyrin having at least one and usually one to four carboxylic acid groups can be activated by reacting with a carbodiimide, 1-hydroxybenzothiazole and an active ester coupling agent, whereby a metallo-porphyrin active ester derivative is obtained which is suitable for coupling to molecules having at least one primary amino group. Particularly, the conjugates obtained by reacting the metallo-porphyrin active ester derivative with the molecule having at least one primary amino group show surprising advantages when used in a detection procedure, e.g. in a procedure for the detection of a biological substance. The conjugates show surprisingly high phosphorescence quantum yields especially in in situ measurements, e.g. in immuno-histochemical, immuno-cytochemical or hybridization measurements. In contrast thereto, conjugates of metallo-porphyrins and biological substances which were prepared by other methods, e.g. in an aqueous solution, did not give any positive results in in situ measurements.

In the process of the invention the carboxylic acid groups of different porphyrin structures are reacted with a mixture of a carbodiimide, preferably a dicyclocarbodiimide, 1-hydroxybenzothiazole and an active ester coupling agent. Usually, this mixture is allowed to react over night and at room temperature, whereby a precipitate of white dicyclo urea crystals, as a by-product, is formed. The active esters of the present invention are prepared in an organic solvent, preferably in a dry organic solvent, such as double distilled DMF to avoid hydrolysis of the active esters due to the reaction with water. The active esters can be stored at −20° C. and they retain their reactivity for at least seven months.

Since the porphyrin starting products (II) can contain several, usually up to 4, carboxylic acid groups, the number of activated carboxylic acid groups can be modified. This can be achieved by varying the molar ratio of the porphyrin (II) and the other reagents. Preferably, the molar ratio of carboxylic acid groups to be activated (n) to carbodiimide to 1-hydroxybenzothiazole to active ester coupling agent is about 1:1:1:1. More preferably, the molar ratio is selected such that an activated metallo-porphyrin derivative is obtained which contains from 2 to 3 activated carboxylic acid ester groups. It should be noted that the number of activated carboxylic acid groups n as defined according to the present invention is a statistical average number, and thus is not necessarily an integer.

In formula (I) the symbol R denotes a chemical bond or a linker group by which the activated carboxylic ester group is bound to the porphyrin structure. For example, the linker group may be an aliphatic, alicyclic and/or aromatic hydrocarbon group, which may contain heteroatoms. Preferably, the linker group is a $C_1$–$C_{20}$ alkylene group which may contain heteroatoms, an arylene group, and aralkylene group or an alkarylene group. More prefereably, R is a chemical bond, a $C_1$–$C_5$ alkylene group or a phenylene group.

For the process of the present invention, metallo-porphyrin starting materials (II) are used which contain at least one carboxylic acid group, preferably at least two carboxylic acid groups and most preferably four carboxylic acid groups. Specific examples for suitable porphyrins are Pt- or Pd-coproporphyrins and uroporphyrins which contain four propionic acid groups or four acetic acid groups, respectively. Further examples for suitable porphyrins are Pd- or Pt-mesoporphyrins, deuteroporphyrins, protoporphyrins, hematoporphyrins and cytoporphyrins having two propionic acid groups. Still, further examples for suitable porphyrins are known to the skilled person in the art.

With regard to the synthesis of metallo-porphyrins, and espescially Pt- and Pd-porphyrins it is referred to The porphyrins, structure and synthesis, Part B (1978), Chapter 10, by J. W. Buchler, Synthesis and properties of metallo-porphyrins, p. 390–483, especially, p. 471–474, Editor: D. Dolphin, Academic Press Inc., London, which is incorporated by reference.

Figure 1:
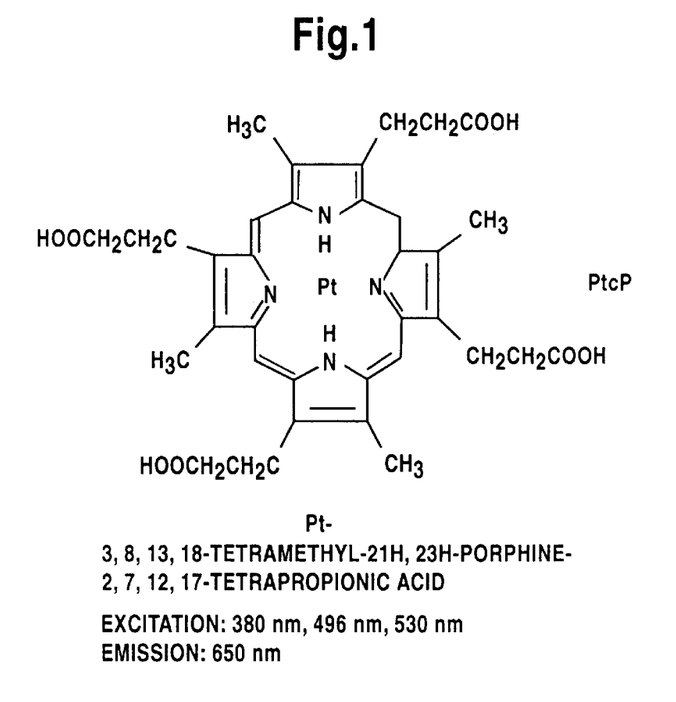
FIG. 1 shows the formula of a preferred metallo-porphyrin which is used as a starting compound for the present invention (PtcP)
Figure 2:
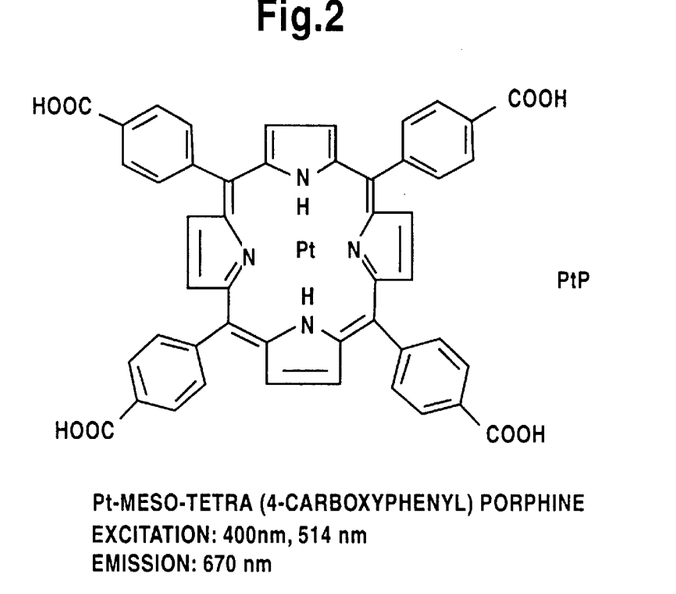
FIG. 2 shows the formula of a further preferred metallo-porphyrin which is used as a starting compound for the present invention (PtP)

Especially preferred examples for suitable metallo-porphyrins are Pd- or Pd-3,8,13,18-tetramethyl-21H,23H-porphine-2,7,12,17-tetra-propionic acid (FIG. 1) and Pd- or Pt-meso-tetra (4-carboxyphenyl) porphine (FIG. 2).

The process of the present invention is conducted in an organic and preferably waterfree solvent. The carbodiimide is a carbodiimide which is soluble in the organic solvent. Preferred are dicyclocarbodiimides such as dicyclohexylcarbodiimide.

The active ester coupling agent is preferably a substance which is soluble in organic solvents such as DMF. Specific examples for suitable active ester coupling agents are N-hydroxysuccinimide, thiophenyl esters, aryl esters and vinyl esters.

A further subject matter of the present invention is an activated metallo-porphyrin derivative having the general formula I:

$$M\ P\text{—}(RCOOX)_n \qquad (I)$$

wherein M, P, R, COOX and n are defined as above. Preferably, n is 2 or 3.

It was shown that the activated metallo-porphyrin derivatives according to the present invention are sufficient reagents to modify primary amino groups. This modification procedure includes a process for the preparation of a metallo-porphyrin conjugate, wherein the activated metallo-porphyrin according to the present invention is coupled to a molecule having at least one primary amino group, whereby at least one bond is formed between an activated carboxylic acid ester group and a primary amino group. Different molecules such as biomolecules or polymers can be coupled to the activated metallo-porphyrin. For example, biomolecules can be selected from the group comprising biogenic amines, hormones, vitamins, metabolites, nucleosides, nucleotides, oligonucleotides, nucleic acids, peptides, polypeptides, glycoproteins, saccharides, lipids, cellular and viral components, cells and viruses. Specific examples of biomolecules are tyramine, allylamine-modified nucleotides, immunoglobulins, immunoglobulin-fragments and avidin. An example of a polymer is an amino-modified polyvinylalcohol ($PVA-NH_2$).

When coupling the activated metallo-porphyrin to molecules having at least one primary amino group, it was found that the active esters of porphyrins, wherein the carboxylic acid group is attached to an aliphatic chain, are more reactive than active esters of porphyrins, wherein the carboxylic acid ester group is attached to an aromatic group. Furthermore, it was found that activated porphyrins containing multiple active ester groups, preferably from 2 to 3, are more reactive than the monoester compounds of a given porphyrin.

For the labelling of biomeolecules, such as proteins, the use of metallo-porphyrin derivatives having from 2 to 3 ester groups, is particularly preferred because then the highest ratio of porphyrin to protein (F/P-ratio) and less interference with avidin/antibodies was found compared to monoester derivatives. Further it was found that the coupling procedure should be carried out with a not too high protein concentration, e.g. a protein concentration up to 5 mg/ml, e.g. an avidin concentration of 1 mg/ml or an IgG concentration of 2 mg/ml. The protein is preferably coupled with a 3 to 6-times excess of porphyrin di- or tri-active ester. The reaction temperatures depend on the reactivity of the activated metallo-porphyrin derivative and are suitable in the range of 0° to 4° C. for porphyrin derivatives wherein the active ester groups are attached to an aliphatic chain and 30° to 40° C. for porphyrin derivatives wherein the active ester groups are attached to an aromatic chain.

A further subject matter of the present invention is a metallo-porphyrin conjugate, wherein a metallo-porphyrin derivative (I) is coupled via at least one activated carboxylic ester group thereof to a molecule having at least one primary amino group. The conjugate according to the present invention is used in a procedure for the detection of a biological substance. This procedure generally comprises a detection of the conjugate by phosphorescence. Preferably the phosphorescence is detected in a time-resolved measurement due to the decay time of the present compounds from 10 to 200 μs, preferably from 50 to 150 μs.

When detecting the phosphorescence of the metallo-porphyrin conjugate by a time-resolved measurement, advantage can be taken of the specific background fluorescence. In this detection scheme pulsed excitation can be used in combination with gated detection of the emission. When applying time-resolved microscopy the lifetime of the metallo-porphyrin conjugated is generally selected in such a way that the specific phosphorescence can be detected in absence of the unwanted background signals.

When using the metallo-porphyrin conjugates of the present invention, a pulse length of the excitation light in the range of 10–100 μs, e.g. about 50 μs, has been suitable. The repetition period of the sequence can be as short as 100 μs, e.g. 100–500 μs, preferably about 250 μs. The detection window can have a length of e.g. 1–100 μs, e.g. about 10 μs in combination with a delay time which is preferably in the range of 5 to 10 μs for use with biological autofluorescing materials or less than 1 μs for use in hybridization assays on membranes.

More specifically, the conjugates of the present invention can be used in immunoassays, nucleic acid hybridization assays and other types of assays such as specific deposition assays.

The conjugates of the present invention are especially suitable for in situ and/or in vitro measurements in an autofluorescing environment, such as tissue sections, whole cells and metaphase preparations. A further example of an autofluorescing environment are autofluorescing membranes such as nitrocellulose or polyvinylidene fluoride membranes.

The conjugates according to the present invention can be used in several different approaches to detect antigens or nucleic acids in in situ applications. One is an enzymatical method based on the deposition of biotin- or metallo-porphyrin labelled tyramides by horseradish peroxidase. Biotin deposits can be detected by metallo-porphyrin labelled avidin. Further, conventional immunofluorescence techniques, using metallo-porphyrin labelled antibodies or -avidins, can be applied.

With the tyramide based method good sensitivity can be reached, both with continuous and time-resolved excitation/detection using different microscopes. It was found that it is possible to visualize targets as small as housekeeping gene mRNAs in cultured cells and cosmid probes on metaphase preparations, without the use of integrating cameras. Specific signals are more intensely stained with directly metalloporphyrin labelled tyramides than obtained with the biotin method. However, the direct method also shows an increased background, especially on tissue sections. This background can, however, be decreased by addition of bovine serum albumin.

Conventional immunofluorescence techniques can also be applied. Without the use of integrating cameras, only relatively high-abundant targets such as 28SrRNA in cultured cells and (middle) repetitive probes on metaphase preparations can be visualized. To reach this, the application of multiple rounds of antibodies/avidin is preferred. For in situ hybridization applications best results are obtained with hapten-labelled probes (e.g. digoxigenin-labelled probes) which can be detected by biotinylated anti-hapten antibodies and metallo-porphyrin labelled avidin. Usually, 3 to 4 incubations with antibodies are preferred to visualize the targets mentioned above. With the use of integrating cameras sensitivity of these multilayer-approaches increases such that for instance also cosmid probes can be detected.

Furthermore, other immunochemical methods such as the appliance of metallo-porphyrin-labelled antibodies and metallo-porphyrin labelled DNA-probes are suitable for immuno histochemical, immunocytochemical and in situ hybridization applications.

Another application for the conjugates of the present invention is oxygen imaging. In the publication Wilson & Cerniglia (Cancer Res. 52(1992), 3988–3993) the localisation of tumors and evaluation of their state of oxygenation by phosphorescence imaging is described. A publication by Vanderkoii et al (Biochemistry 29, (1990) 5332–5338) discloses an examination of oxygen gradients in mitochondria with delayed luminescence from excited-state triplet probes. These measurements are based on an oxygen-dependent quenching of phosphorescence which enables to image the distribution of oxygen pressure in tissue environments such as tumors or mitochondria. When using the conjugates according to the present invention, superior results compared to conjugates according to the prior art can be obtained.

Further, the present invention shall be explained in more detail by the following drawing and examples:

The drawing consists of 3 Figures.

EXAMPLES

1. Preparation of PtP- and PtcP-NHS esters

Figure 3:
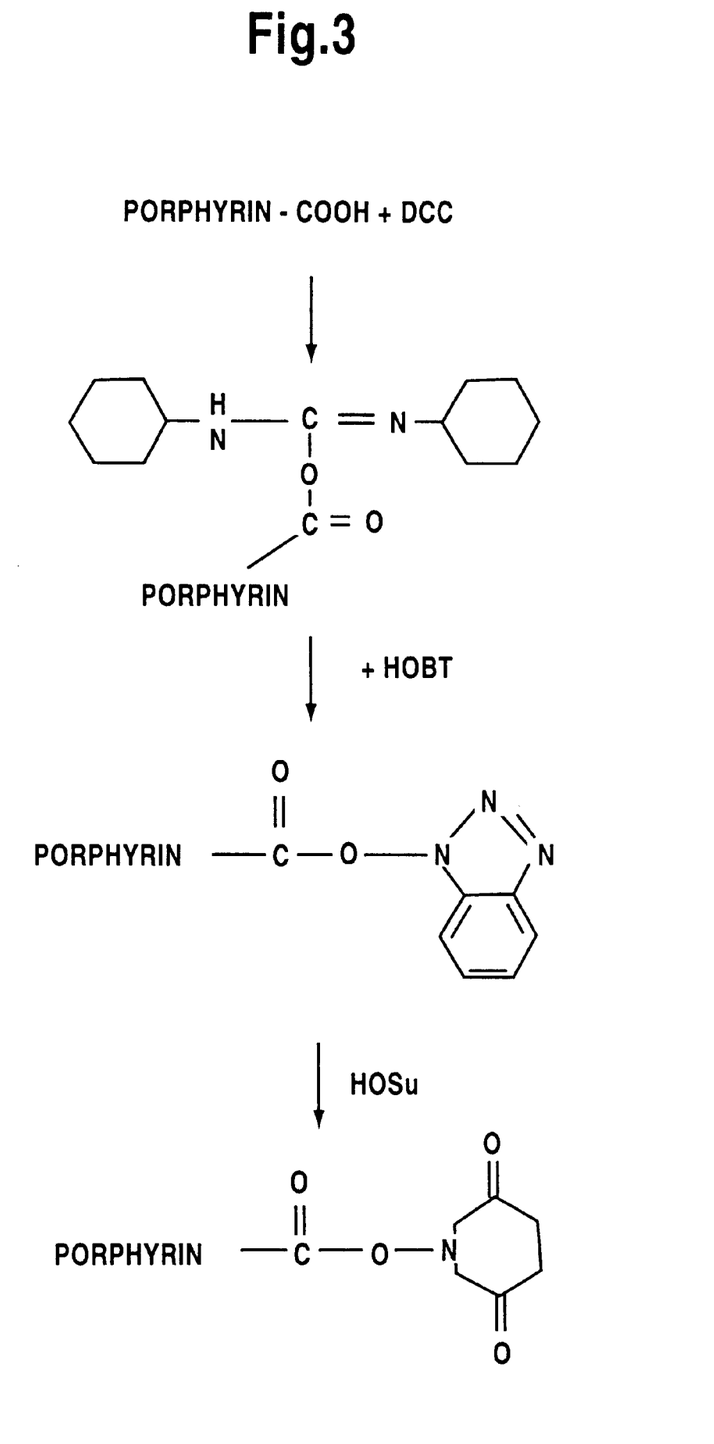
FIG. 3 shows a reaction pathway for conducting the process of the present invention.

N-hydroxy succinimide ester (NHS) derivatives of Pt-meso-tetra (4-carboxyphenyl)porphine (PtP FIG. 2)) and 3,8,13,18-tetramethyl-21H,23H-porphine-2,7,12,18-tetrapropionic acid (PtcP FIG. 1)) were synthesized by reacting equimolar amounts of COOH, N-hydroxysuccinimide (Aldrich), DCC (dicyclocarbodiimide, Pierce) and HBTO (1-hydroxy benzothiazole, Aldrich) in dry DMF. An urea precipitate was formed during an overnight incubation at room temperature (RT). The NHS ester derivatives were used without further purification. The reaction pathway is depicted in FIG. 3.

The respective amounts of reagents to prepare the following NHS derivatives were:

| | Pt-porph. mg | HBTO mg | DCC mg | NHS mg | vol. ml | PtP-NHS [mM] |
|---|---|---|---|---|---|---|
| PtP mono NHS ester PtP-1-NHS | 19.3 | 2.7 | 4.1 | 2.3 | 2.8 | 7.0 |
| PtP di/tri NHS ester PtP-2.5-NHS | 26.6 | 11.2 | 7.3 | 6.2 | 12.0 | 2.2 |
| PtcP mono NHS ester PtcP-1-NHS | 20.6 | 5.0 | 3.3 | 2.8 | 1.13 | 18.7 |
| PtcP di NHS ester PtcP-2-NHS | 17.9 | 8.7 | 5.7 | 4.9 | 1.24 | 17.0 |
| PtcP tri NHS ester PtcP-3-NHS | 10.8 | 7.9 | 5.2 | 4.4 | 0.78 | 17.7 |
| PtcP tetra NHS ester PtcP-4-NHS | 10.8 | 10.5 | 6.9 | 5.9 | 0.79 | <17.5 |

2. Preparation of PtP- and PtcP-Labelled Antibody Conjugates

2.1. Preparation of Goat Anti-DIG IgG PtP-Conjuqates

The total IgG fraction of a goat IgG anti DIG antiserum was purified first by ammoniumsulphate precipitation, followed by purification with a Superdex 200 column (Pharmacia) using 1× NHS buffer as an eluent. IgG was labelled either with PtP-NHS or fluorescein-NHS. For the PtP labelling IgG was labelled at a IgG concentration of 2 mg/ml (13.33 $\mu$M) in 1× NHS buffer with either 33, 83, 132 or 220 $\mu$M PtP-2.5-NHS or with 47, 83, 140 or 210 $\mu$M PtP-1-NHS. The reaction was allowed to proceed for 16 hrs on ice. Purification was performed by gelfiltration on Sephadex G50f with PBSE as an eluent.

| NHS-ester | PtP:IgG | F/P[1] | activity[2] (%) |
|---|---|---|---|
| PtP-2.5-NHS | 2.5 | 1.9 | 84 |
| " | 6.2 | 4.9 | 42 |
| " | 9.9 | 6.8 | 25 |
| " | 16.3 | 7.6 | 15 |
| PtP-1-NHS | 3.0 | 2.0 | 42 |
| " | 6.0 | 4.4 | 23 |
| " | 9.0 | 5.0 | 21 |
| " | 13.5 | 6.8 | 12 |

[1] F/P = Pt-porphine:IgG ratio = 0.9 $A^{397}/(A^{280} - 0.35 A^{397})$
[2] Activity of the protein in OD495 per $\mu$M labelled IgG/OD495 per uM unlabelled IgG × 100% From anti-DIG ELISA

2.2. Preparation of Goat Anti-Mouse Antibody PtcP-Conjugates

A 1 mg or 434 $\mu$l goat IgG anti-mouse IgG (Pierce, anti mouse IgG H+L, affinity isolated antibody, 2.3 mg/ml in 10 mM phosphate pH 7.6, 0.25 M NaCl) was treated with 1.4 or 2.5 $\mu$l PtcP-3-NHS (17.7 mM in DMF). Reaction was allowed to proceed for 2 hrs on ice and purified by gelfiltration (Seph. G50f, PBSE). Typical yields of IgG were >95%.

B 1 mg or 770 $\mu$l goat anti-mouse IgG (Pierce, F(ab')$_2$ fragment of affinity isolated IgG, 1.3 mg/ml in 10 mM phosphate pH7.6, 0.25 M NaCl) was treated with 2.3 $\mu$l PtcP-3-NHS ester. Reaction was allowed to proceed for 2 hrs on ice and purified by gelfiltration (Seph. G50f, PBSE). Yield of F(ab')$_2$ was 93.2%.

C The total IgG-fraction of goat anti-mouse (GaM) antiserum was dialysed against PBS (pH 7.7) and labelled at a protein concentration of 1.8 mg/ml (12 μM). To 1 mg (±0.5 ml) IgG either 1 or 2.5 μl PtcP-3-NHS was added. The reaction was allowed to proceed for 1.5 hrs. on ice and purified by gelfiltration (Seph. G50f, PBSE). Typical yields of IgG were >85%.

| method[1] | PtcP:IgG | F/P[2] | activity[3] (%) |
|---|---|---|---|
| A | 3.8 | 2.9 | >95 |
| A | 7.1 | 6.0 | >95 |
| B | 3.7 | 2.5 | >95 |
| C | 7.4 | 7.0 | >95 |
| C | 3.0 | 2.6 | >95 |

[1]Method A, B or C as described above.
[2]F/P (IgG) = Pt-coproporphine:IgG ratio = $3.8A^{380}/(A^{280} - 0.3A^{380})$
F/P (Fab'$_2$) = $2.5A^{380}/(A^{280} - 0.3A^{380})$
[3]Activity of the protein in % is OD495 per μM labelled IgG/OD495 per μM unlabelled protein × 100% as obtained from the GaM ELISA assay.

All PtP- or PtcP-labelled antibodies were tested in IHC and ISH assays (Example 8). Either a monoclonal antibody was detected by GaM conjugates or DIG-labelled probes were detected by goat anti-DIG-PtP conjugates. Upon continuous fluorescence using the DM microscope (green or violet excitation) no specific fluorescence was observed. By using rat anti-goat-FITC conjugates as a third/second layer it was shown that these antibodies had specifically bound but were not detected. Also the fluoresceinated antibodies, labelled together with the PtP conjugates, showed both good labelling and specific (and sensitive) detection of mouse IgG or DIG-probes.

3. Avidin-D Conjugates

Avidin-D obtained from Vector was used as a source of avidin.

It has an isoelectric point of ±7.5 and contains no carbohydrates.

F/P ratios were measured either by UV/VIS spectroscopy or by using BCA reagent (Pierce) to measure avidin concentrations combined with measurements in a spectrophotometer at 397 nm (PtP) or 380 nm (PtcP).

Formulas to calculate F/P ratios:
Avidin-D-PtP: $1.1 A^{397}/(A^{280} - 0.4 A^{397})$
Avidin-D-PtcP: $1.7 A^{380}/(A^{280} - 0.3 A^{380})$

3.1. Preparation of Avidin-PtcP and Avidin-PtP Conjugates

Avidin-D was labelled as a 2 mg/ml solution in 1× NHS buffer (30 μM). Labelling was performed with PtP-1/2.5-NHS and PtcP1,2 or 3-NHS and allowed to proceed for 16 hrs on ice. Purification was done with standard gel filtration.

5× NHS buffer

This buffer contains: 0.25 M Na-phosphate pH8.0

0.5 M NaCl 25 mM EDTA pH8.0
1. Prepare 500 ml 0.5 M Na-phosphate pH8.0.
2. Add 100 ml 5 M NaCl and 50 ml 0.5 M EDTA pH8.0.
3. Autoclave 20 min. at 120° C.
4. Adjust volume to 1 liter with autoclaved bidestillated water.

The following conjugates were obtained:

| label | Pt(c)P:Avidin | yield (%) | F/P |
|---|---|---|---|
| PtcP-1-NHS | 2 | 67 | 2.0 |
|  | 4 | 46 | 3.3 |
|  | 8 | 23 | 7.4 |
| PtcP-2-NHS | 2 | 68 | 2.2 |
|  | 4 | 41 | 3.3 |
|  | 8 | 15 | 7.3 |
| PtcP-3-NHS | 2 | 70 | 2.3 |
|  | 4 | 49 | 3.1 |
|  | 8 | 15 | 6.8 |
| PtP-1-NHS | 2 | 67 | 0.1 |
|  | 4 | 40 | 0.3 |
|  | 8 | 24 | 0.6 |
| PtP-2.5-NHS | 2 | 72 | 0.2 |
|  | 4 | 55 | 0.4 |
|  | 8 | 31 | 0.8 |

From the PtcP labels all conjugates made with a 2 times excess were pooled and concentrated over Centricon30 cut off filters (avidin-PtcP A, 3.9 mg/ml, F/P 2.2). Also all 4 times excess samples (avidin-PtcP B, 1.1 mg/ml, F/P 3.2) and all 8 times excess samples were pooled (avidin-PtcP C, 0.33 mg/ml, F/P 7.1).

The 3 PtcP conjugates were tested in the Biotin ELISA assay. The data showed that the PtcP conjugates A retained 82%, B 68% and C 43% of their original activity (OD490/ng avidin).

3.3 Avidin-PVA-PtP Conjugates

Preparation of PtP- and Biotin-Labelled Polyvinyl Alcohol (PVA)

1. To 11.5 mg PVA-NH$_2$ (⅓ OH=NH$_2$; 0.4 ml in DMSO), 50 μl triethylamine (TEA) was added and either 0.5 ml PtP-1-NHS ester (7 mM)+50 ul 10 mM biotin-LC-NHS ester (Pierce in DMSO) was added to obtain PtP1B15 (15% of the NHS esters contained a biotin) or 0.5 ml PtP-2.5-NHS ester (2.2 mM)+25 μl 10 mM biotin-LC-NHS ester in DMSO was added to obtain PtP2B20. The incubation was 18 hrs at 60° C.

2. After addition of 4 ml bidestillated water to each sample, the labelled PVA molecules were purified using 2 Centricon 100 filters (Amicon) per sample. 1× TE was used to wash the >100 kDa product. They were spun 3×90 min. 3000 rpm in a Sorvall centrifuge at 4° C. Yields were 2×50 μl PtP1B15 (very dark coloured) or 2×500 μl PtP2B20 (orange). Using the mono NHS ester more product appeared <100 kDa than obtained with the di NHS ester. It was found that biotinylated PVA >100 kDa provides superior results over <100 kDa PVA.

Preparation of PtP-PVA-Avidin-D Conjugates

3. The PtP/biotin labelled PVA >100 kDa products were treated with avidin-D to prepare avidin-PVA-PtP conjugates by affinity chemistry. For this, 0.5 mg avidin-D in 100 μl 4× SSPE was added to 100 μl PtP1B15 or 1 mg avidin-D in 200 μl 4× SSPE was added to 1 ml PtP2B20. The samples were allowed to react 2 hrs at 30° C. after which the volume of both samples was brought to 1.5 ml using PBSE (PBS+2 mM EDTA). The colour of both samples was brown.

4. The samples were purified from unbound avidin-D using Centricon 100 filters (3×90 min. 3000 rpm against PBSE). Tests with avidin-D only showed a yield of <1%, indicating that with this method all unbound avidin-D is removed. Yields were:

APP1: 0.2 ml Avidin-PtP1B15, dark brown coloured.

APP2: 1.0 ml Avidin-PtP2B20, orange coloured.

Products <100 kDa showed little colour (APP1) or almost no colour at all (APP2).

4. ELISA Experiments

4.1. Anti-DIG ELISA

Goal of this ELISA is to determine the digoxigenin (DIG) binding activity of porphyrin labelled goat IgG anti-DIG (GaDIG) antibodies. DIG is coated to the plate and incubated with a serial dilution of different GaDIG conjugates using similar serial dilutions of unlabelled GaDIG as a 100% control. The amount of bound (=immunoactive) goat IgG per mass unit IgG is measured by incubating with horseradish peroxidase (HRP) labelled anti-goat IgG antibodies. The HRP is analytically determined with o-phenylenediamine (OPD).

1. Coat 96-well plate (Greiner) 2 hrs at 37° C. with 150 μl 10 μg/ml DIG labelled rabbit IgG (1:500) in 0.1 M Na-carbonate pH 10. Wash the plate 3× with TNT (50 mM TrisHCl pH 7.4, 0.15 M NaCl, 0.05% Tween 20).
2. Incubate with 150 μl TNB (50 mM TrisHCl pH 7.4, 0.15 M NaCl, 0.5% (w/v) blocking agent (Boehringer Mannheim)) for 30 min. at 37° C.
3. Incubate 1 hr at 37° C. with 100 μl of the GaDIG conjugates (unlabelled GaDIG is 100% control). Best results were obtained with a 2-fold serial dilutions in TNB, starting with 50 μg/ml IgG. Wash the plate 3× with TNT.
4. Incubate 1 hr at 37° C. with 125 μl rabbit anti-goat antibody-HRP conjugate (Sigma, 1:2500), diluted in TNB. Wash the plate 3× with TNT.
5. Incubate at least 30 min. at RT with 150 μl 0.4 mg/ml OPD in OPD buffer (0.1 M citrate/phosphate pH 5.3) containing 0.03% $H_2O_2$. Stop reaction with 50 μl 0.18 M $H_2SO_4$. Read optical density (OD) at 492 nm.

4.2. GaM ELISA

Goal of this ELISA is to determine the mouse IgG binding activity of porphyrin labelled goat IgG anti-mouse IgG (GaM) antibodies. Mouse IgG is coated to the plate and incubated with a serial dilution of different GaM conjugates using similar serial dilutions of unlabelled GaM as a 100% control. The amount of bound (=immunoacitve) goat IgG per mass unit IgG is measured by incubating with HRP labelled anti-goat IgG antibodies. The HRP is analytically determined with OPD.

1. Coat 96-well plate (Greiner) 2 hrs at 37° C. with 150 μl 10 μg/ml mouse IgG (Sigma) in 0.1 M Na-carbonate pH 10. Wash the plate 3× with TNT.
2. Incubate with 150 μl TNB for 30 min. at 37° C.
3. Incubate 1 hr at 37° C. with 100 μl of the GaM conjugates (unlabelled GaM is 100% control). Best results were obtained with a 2-fold serial dilutions in TNB, starting either with 50 μg/ml IgG (if total IgG fraction of the antiserum is used) or with 10 μg/ml IgG (if the affinity isolated IgG fraction of the antiserum is used). Wash the plate 3× with TNT.
4. Incubate 1 hr at 37° C. with 125 μl rabbit anti-goat IgG-HRP (Sigma, 1:2500), diluted in TNB. Wash the plate 3× with TNT.
5. Incubate at least 30 min. at RT with 150 μl 0.4 mg/ml OPD in OPD buffer containing 0.03% $H_2O_2$. Stop reaction with 50 μl 0.18 M $H_2SO_4$. Read optical density (OD) at 492 nm.

4.3. Biotin ELISA

Goal of this ELISA is to determine the biotin binding activity of porphyrin labelled avidin-D. Biotinylated BSA is coated to the plate and incubated with serial dilutions of different avidin-D conjugates using similar serial dilutions of unlabelled avidin-D as a 100% control. The amount of bound avidin-D per mass unit avidin-D is analytically determined by incubating with HRP labelled anti-avidin-D antibodies. The HRP is analytically determined with OPD.

1. Coat 96-well plate (Greiner) 2 hrs at 37° C. with 150 μl 10 μg/ml biotinylated BSA (20 mg/ml stock, BSA was labelled at 20 mg/ml for 2 hrs at 30° C. with 5 mg/ml biotin-LC-NHS obtained from Pierce, dissolved in DMSO as 50 mg/ml stock) in 0.1 M Na-carbonate pH 10. Wash the plate 3× with TNT.
2. Incubate with 150 μl TNB for 30 min. at 37° C.
3. Incubate 1 hr at 37° C. with 100 μl of the avidin-D conjugates (unlabelled GaM is 100% control). Best results were obtained with a 2-fold serial dilutions in TNB, starting with 200 μg/ml avidin-D. Wash the plate 3× with TNT.
4. Incubate 1 hr at 37° C. with 125 μl goat anti-avidin-D-HRP (Vector, 1:400), diluted in TNB. Wash the plate 3× with TNT.
5. Incubate at least 30 min. at RT with 150 μl 0.4 mg/ml OPD in OPD buffer containing 0.03% $H_2O_2$. Stop reaction with 50 μl 0.18 M $H_2SO_4$. Read optical density (OD) at 492 nm.

6. Preparation of PtP- and PtcP-Labelled Tyramides

6.1. DCC/HBTO method (comparative)

The carboxyl groups of PtP were reacted with the amino group of tyramine (Tyr). PtP-$(COOH)_4$ (8 mM) was reacted with 1, 2 . . . 4 times excess of DCC, HBTO and 0, 1 . . . 4 excess tyramine in freshly opened DMSO.

The tyramides were tested by a CD4 detection on lymphocytes in concentrations of 8 and 80 μM. The no tyramide control showed a relatively high background on all lymphocytes. No specific detection was observed with the different PtP-Tyrs.

Then the same method was applied to prepare PtP-$(COOH)_2(Tyr)_2$. The reaction was now performed in DMF and done in 2 steps: 1. reaction with DCC and HBTO (PtP:DCC,HBTO=2:1) then 2. reaction with tyramine (PtP:Tyr=2:1). The first reaction was performed at different incubation times. These tyramides were tested at 20 μM, by an in situ hybridization on lymphocyte chromosomes. No results were obtained.

6.2. Mixed Anhydride Method (Comparative)

PtP was reacted with triethylamine (TEA), ethylchloroformate (ECF) and tyramine. DMF was used as a solvent. PtP:TEA, ECF or Tyr was 2:1. These tyramides were tested at 20 μM, by an in situ hybridization on lymphocyte chromosomes. No results were obtained.

6.3. DCC/HBTO NHS Method (Invention)

PtP- and PtcP-NHS esters were prepared according to Example 1 and then reacted with tyramine in DMF+ 0.3–10% TEA. Incubations were performed overnight at 42° C. or 4 hrs at 50° C. The samples were stored at −20° C. and tested in a filter assay. Mouse IgG was spotted 1 ng 1:3 100 fg in 0.1% BSA onto hybond Cextra. Using TNB to block/ dilute antibodies and TNT to wash in between incubation steps, mIgG was detected by sheep anti-mouse DIG-conjugate (1:2500) and sheep anti-DIG HIRP-conjugate (1:1000). The tyramide detection was carried out at pH 8.0/0.003% $H_2O_2$ and a concentration of 50 μM. All prepared tyramides detected ±10 pg (absorbance).

The tyramides prepared were:

| Description | NHS ester used | [PtP] mM | [NHS] mM | [Tyramid] mM |
|---|---|---|---|---|
| PtP(COOH)$_3$(Tyr)$_1$ | PtP-1-NHS | 5.5 | 5.5 | 4.5 |
| PtP(COOH)$_2$(Tyr)$_2$ | PtP-2.5-NHS | 1.8 | 4.5 | 4.5 |
| PtP(COOH)$_3$(Tyr)$_1$ | PtP-2.5-NHS | 1.8 | 4.5 | 1.8 |

-continued

| Description | NHS ester used | [PtP] mM | [NHS] mM | [Tyramid] mM |
| --- | --- | --- | --- | --- |
| PtcP(COOH)$_3$(Tyr)$_1$ | PtcP-1-NHS | 14.5 | 14.5 | 16.3 |
| PtcP(COOH)$_2$(Tyr)$_2$ | PtcP-2-NHS | 11.6 | 23.2 | 22.9 |

In a filter test the sensitivity of multi-tyramide labelled Pt-porphyrins was better than the sensitivity of single tyramide labelled Pt-porphyrins.

7. Preparation of PtP- and PtcP-Labelled DNA Probes

DNA was labelled with Pt-porphyrin NHS esters using 2 methods.

7.1. Nick-translation with PtP/PtcP-dUTP.

7.2. Nick-translation with allylamine-dUTP, followed by an incubation with PtP/PtcP-NHS ester.

Preparation of Pt-porphyrin-dUTP

To allylamine-dUTP a 5 times excess of PtP- or PtcP-1-NHS ester was added (total: 1× NHS buffer, 10–25% DMF), and incubated 1–4 hrs at 37° C.

PtP-dUTP and PtcP-dUTP were purified by thin-layer chromatography. Kieselgel HPTLC 254 nm plates were used as solid phase and 70% ethanol, 30% H$_2$O was used as an eluent. Rf values found:

| | |
| --- | --- |
| PtP-2.5-NHS (after incubation) | Rf = 0.95 |
| PtP-dUTP (1 PtP/dUTP) | 0.80–0.85 |
| allylamine-dUTP | 0.2 |
| N-hydroxysuccinimide | 0.85 |

Preparation of NH$_2$-Labelled DNA and Labelling with Pt-porphyrin-NHS.

DNA probes were labelled with primary amino groups. For this a standard nick-translation was done. The nick-mixture contained amongst others: 50 µM DATP, dCTP, dGTP and 54 µM allylamino-dUTP (1/50 2.7 mM stock). The DNA was purified and concentrated by ethanol precipitation. The pellet was dissolved in 1× NHS buffer and reacted with PtP/PtcP-NHS esters. The probe was then purified by gel filtration followed by an ethanol precipitation in the presence of carrier DNA.

8. Immunohisto/Cytochemical (IHC) and in situ Hybridisation (ISH) Experiments 8.1. Tyramide Based IHC The biotin tyramide (BT) detection of HRP for the immunochemical detection of antigens with Pt-porphyrin labelled avidin-D was tested in 2 different assays. Firstly, vimentin was immunologically stained in 4 µM rat liver cryostat sections obtained from rats that were injected with polymeric rat IgA complexes. After an acetone fixation for 10 min. at RT, the sections were incubated for 1 hr at 37° C. with mouse IgG anti vimentin (Amersham RPN 1102, diluted 1:40 in TNB), washed 3×5 min. in TNT and incubated for 30 min. at 37° C. with HRP-labelled anti-mouse antibody-avidin complexes diluted 1:250 in TNB. After 3×5 min. washes in TNT, the slides were rinsed in 0.15 M NaCl. Then 0.5 ml tyramide detection solution was applied and incubated for 30 min. at RT. The detection buffer consisted of 20 µM BT, 0.2 M TrisHCl pH 7.5, 10 mM imidazole and 0.001% H$_2$O$_2$. Biotinylated tyramides were detected by Avidin-D labelled with PtP or PtcP (incubation 30 min. 37° C., diluted in TNB). Then the samples were washed 3×5 min. at RT in TNT, dehydrated and embedded in Vectashield®.

Different CD markers were detected on 1% formaldehyde fixed human mononuclear white blood cells. Mouse IgG monoclonal antibodies against CD4, 9, 13, 14 and 19 (Dakopatts, Beckton and Dickinson) were incubated on cytospin preparations of the cells. The slides were subsequently incubated with HRP labelled goat anti-mouse IgG antibody-avidin complexes. Antibody incubations and washes were carried out in TNB and TNT respectively. The detection was performed as described for tissue sections.

8.2. Tyramide Based Phosphorescence in situ Hybridization (PHISH)

Human metaphase preparations were used as a target for tyramide based PHISH. Methanol/acetic acid fixed lymphocyte preparations were dropped onto slides, dried for 2 min. and dipped in 70% acetic acid. The slides were allowed to dry overnight. Then the slides were treated 15 min. at 37° C. with 0.1 mg/ml RNase A (Promega) in 2× SSPE (cf. Sambrook et al, Molecular Cloning. A Laboratory Manual, Second Ed., 1989, Cold Spring Harbor Laboratory Press, B.13), washed twice 5 min. with PBS and once 5 min. at 37° C. with 0.01 M HCl. Then they were incubated for 10 min. at 37° C. in 0.05% (w/v) pepsin (Sigma)/0.01 M HCl, washed twice in PBS and postfixed 10 min. at RT in 1% formaldehyde/PBS. After two washes in PBS the slides were dehydrated through an alcohol series and dried. Both low complexity probes (plasmids) and high complexity probes (cosmids, chromosome libraries) were used. Plasmid probes (specific for the 28S rRNA genes) were denatured and hybridized in a mixture containing 50% formamide, 2× SSPE, 10% dextran sulphate, 0.3–1 ng/µl probe and 50 ng/µl herring sperm DNA. Chromosome libraries and cosmid probes were denatured by incubating them 10 min. at 80° C. in 50% formamide, 2× SSPE, 10% dextran sulphate. The mixtures further contained a 10 times (libraries) or 50 times (other) excess of human Cot1 DNA (Boehringer). The probe was allowed to preanneal to the Cot1 DNA by incubating the mixture 60 min. at 37° C. The slides were denaturated by incubating them 2 min. at 80° C. They were then washed 2 min. in 70% EtOH (−20° C.) and subsequently dehydrated. The preannealed probe/Cot1 mixture was then added and hybridized in the same mixture containing 10 ng/µl labelled probe and 100–500 ng/µl human Cot1 DNA. Hybridization was done 16–20 hrs at 37° C. The slides were subsequently washed once at RT and 2×5 min. at 60° C. in 2× SSPE/0.1% Tween 20 (Sigma), followed by two 5 min. washes in 0.1× SSPE at 60° C.

Biotinylated or digoxigenin labelled probes were prepared by nick-translation and immunochemically detected with streptavidin-HRP (Vector, 5 µg/µl in TNB) or sheep-anti digoxigenin-HRP (Boehringer, diluted 1:200 in TNB). Better results were obtained by 2-step immunological detection of the probes by either mouse-anti-biotin (Sigma, 1:50)+rabbit-anti-mouse-HRP (DAKO, 1:150) for biotinylated probes or mouse-anti-DIG-biotin (Sigma, 1:200)+streptavidin-HRP (Vector, 1:100). Antibodies were incubated 30 min. at 37° C. and washed 3×5 min. in TNT. Tyramide detection was performed as described for tissue sections, except that 20% w/v dextran sulphate was added to the detection mixture. The dextran sulphate concentration in the substrate buffer was lowered to 5% (w/v) when libraries were used as a probe. Finally, if high-repetitive sequence specific probes (e.g. centromere specific probes) were used, 10% PVA (Mw 72KDa) was added in stead of dextran sulphate.

After the final TNT wash the slides were incubated 10 min. at RT in TNT containing 10 ng/µl of the blue fluorescent DNA counterstain diamino propidium iodine (DAPI)

and subsequently dehydrated through an alcohol series. The slides were embedded either in Vectashield® or in Merckoglas® (1:1 diluted with xylene, polymerized at least 30 min. at 37° C.).

8.3. Conventional PHISH

Hybridization and post-hybridization washes were performed as described above. Probe concentrations for plasmid probes were raised to 5–10 ng/µl and cosmids were hybridized at 20 ng/µl+1 µg/µl Cot1-DNA.

Usually a three or four step immunochemical approach was used to visualize PHISH signals on metaphase preparations. Probes were labelled with fluorescein-12-dUTP, Dig-11-dUTP or Estradiol-11-dUTP by nick-translation and immunologically detected by either mouse-anti-DIG (Sigma, 1:200), rabbit-anti-FITC (DAKO, 1:100) or rabbit-anti-estradiol (Boehringer 1:250). For the three step approach slides were incubated with either sheep anti-mouse-biotin-conjugate (Boehringer, 1:200) or goat anti-rabbit-biotin conjugate (Sigma, 1:400), followed by an incubation with avidin-D-PtP/PtcP. All dilutions were in TNB and incubations were 30 min. at 37° C. In between steps the slides were washed 3×5 min. in TNT.

Biotinylated probes were detected by 1. Avidin-PtcP, 2. goat-anti-avidin-D biotin conjugate (Vector, 1:100) and 3. Avidin-PtcP. All dilutions were in TNB and incubations were 30 min. at 37° C. In between steps the slides were washed 3×5 min. in TNT.

Digoxigenin labelled probes were also detected by a four step approach. After an incubation with mouse anti-DIG biotin conjugate, the slides were incubated with the 3 layers as described for the biotinylated probes.

After the final TNT wash the slides were incubated 10 min. at RT in TNT containing 10 ng/µl DAPI and subsequently dehydrated through an alcohol series. The slides were embedded in Vectashield®.

8.4. mRNA Detection

Different in vitro cultured cell lines were used to detect various mRNAs.

Rat9G cells (contains part of the human CMV-IEA gene)
HelaX1 cells (contains the luciferase gene)
Hela cells After the medium had been discarded, the cells grown on microscopic slides were washed twice with PBS and subsequently fixed for 20 min. at RT in 4% formaldehyde, 5% acetic acid, 0.9% NaCl. The cells were then washed with 70% ethanol and stored in this solution at 4° C.

The slides were dehydrated through an ethanol series and washed 10 min. at RT in histoclear® or xylene to remove lipids. After a wash in 100% ethanol the slides were rehydrated with 90% and 70% ethanol. They were than washed in 0.01 M HCl and incubated 1 min. in 0.1% pepsin/0.01 M HCl at 37° C. After a short rinse in bidestillated water the slides were dehydrated through an ethanol series.

The hybridization mixture (60% formamide, 2× SSC (cf. Maniatis et al, Supra, B.13), 10% dextran sulphate and 5 ng/µl DIG labelled probe) was applied. Probe and target were denaturated 2.5 min. at 80° C. and hybridization was allowed to proceed for 16–20 hrs. at 37° C. The slides were washed 5 min. in 2× SSC at RT to remove the coverslips and then 3×5 min. in 60% formamide, 2× SSC at 37° C.

The immunochemical detection was performed as described above.

8.5. Detection of glutathione-S-transferase (GSTP) on Technovit®8100 Embedded Rat Liver Sections Liver biopts were fixed 2 hrs. at RT in 2% paraformaldehyde, followed by an overnight incubation in sucrose. The liver was then embedded in Technovit®8100.

Sections of 4 µm were cut and placed on ethanol/ether (1:1) cleaned slides. The slides were stored at 4° C.

The slides were dried 2 hrs. at 37° C. and treated 5 min. at 37° C. with 0.01% trypsin (Boehringer) in 0.1 M TrisHCl pH 7.8/0.1% $CaCl_2$. After two 10 min. washes in PBS the slides were incubated 15–30 min. in TNB at 37° C., before a rabbit-anti-rat GSTP polyclonal antibody was applied (diluted 1:150 in TNB). After an incubation of 2 hrs. at 37° C., the slides were washed 3×5 min. in PBS and treated 30 min. at 37° C. with goat-anti-rabbit antibody HRP conjugate (Sigma, diluted 1:200 in TNB). After 3×5 min. washes in PBS, the BT reaction was performed as described above without PVA or dextran sulphate and after 30 min. at RT, washed 3×5 min. in PBS and the biotin deposits were immunochemically detected by avidin-PtP (30 min. at 37° C. in 30–50 µg/ml in TNB). After 3×5 min. washes in PBS, the sections were dried through an ethanol series and embedded in Merckoglas®.

9. Biotin Tyramide Based Immuno Histo/ cytochemical and in situ Hybridization Assay

9.1. GSTP Detection in Rat Liver Sections (Technovit®8100 Embedded)

The sections were embedded in plastic (Technovit®8100). A high autofluorescence of the sections was observed using different filtersets on the microscope. GSTP protein was immunochemically detected by a 2 step method: first a rabbit anti-GSTP antibody followed by goat-anti-rabbit antibody-HRP conjugate. After the reaction with biotin-tyramide conjugate, the biotin deposits were then stained by avidin-PtP. The results showed that using the time-resolved microscope GSTP could easily detected by the Pt-porphyrin labelled avidin with a complete black background. Signal to noise ratios were far superior to the results obtained with fluoresceinated antibodies.

9.2. RNA PHISH CMV-mRNA Detection on Rat9G Cells pSS, a 7 kb plasmid probe specific for the immediate early antigen of human cytomegalovirus (CMV), was labeled with digoxigenin-11-dUTP and used as a probe to detect the CMV mRNA present in 10–30% of cycloheximide stimulated Rat9G cells. The hybridized probe was immunochemically detected by sheep-anti-DIG antibody-HRP conjugate (diluted 1:100), followed by a reaction with biotin. Biotin deposits were then stained by avidin-PtP.

A signal was observed in about 20% of the cells. The signals were both visualized by eye using a normal fluorescence DM microscope (Leica) and by time-resolved microscopy using an CCD camera (CH250, Photometrics Ltd., Tucson, USA).

10. Biotin Tyramide Based IHC and ISH with PtcP Labelled Avidin-D

10.1. PHISH on Human Metaphase Preparations

Probes of different target size were used to perform time-resolved PHISH with samples embedded in Vectashield® (10.1–10.4). These included different chromosome centromere specific probes specific for human satellite III DNA or alpha repeats. Furthermore, a probe specific for the 28S ribosomal genes, different cosmids and chromosome libraries were used.

All mentioned probes were easily detected. Signals could be viewed by fluorescence using a DM microscope or different microscopes suitable for time-resolved fluorometry.

Different immunological methods were tested for the combination of BT and avidin-PtP/PtcP using cosmids specific for the short arm of chromosome 2 (carbamoyl-P-synthetase-aspartate transcarbamoylase-dihydroorotase (CAD) gene) or chromosome X (Duchenne muscular dystrophy (DMD) gene).

When using a biotin probe label, especially good results were obtained with mouse-anti-biotin (Sigma) and rabbit anti-mouse HRP conjugate (DAKO). When using a digoxigenin probe label, especially good results were obtained with mouse anti-DIG biotin conjugate (Sigma) and Streptavidin-HRP-conjugate (Vector).

With these methods it was possible to detect any target on human metaphase preparations. The sensitivity was better than conventional immunology with fluorescein- or rhodamine-labelled probes/antibodies.

Targets with a high copy number (e.g. centromeric probes) were incubated in BT with 10% (w/v) PVA (72 kDa) and the other probes in BT with 15–25% (w/v) dextran sulphate. This was done to ensure optimal resolution of the signals.

10.2. Double Hybridisation on Basis of Time-Resolved Fluorometry

A double ISH experiment on human metaphase preparations was performed. Rhodamine-4-dUTP (Boehringer) labelled plasmid pUC1.77 (a pUC plasmid containing a 1.77 kb insert specific for human satellite III DNA located on chromosome 1 band 1q12) specific for chromosome 1 (c#1) was cohybridized with a DIG labelled 28S rDNA probe. The DIG probe was detected by HRP labelled anti-DIG Fab-fragments, stained with BT and the biotin deposits were detected by avidin-PtcP.

Results obtained from continuous fluorescence showed positive staining of c#1 and on the short arms of all acocentric chromosomes (28S rDNA genes). The targets eventually stained by PtcP were more dark red than the rhodamine stained targets. Upon time-resolved fluorometry (laser microscope) the 28S signals were still strongly visible but the c#1 signals were no longer detectable. This shows that the PtcP signals were still time-resolved and background subtraction using this microscope is high.

10.3. mRNA Detection

Different mRNA sequences were detected by time-resolved ISH and the BT system. HelaX1 cells were used and rRNA, human elongation factor (HEF)-mRNA and Luciferase-mRNA were successfully detected by BT/avidin-PtcP using DIG labelled probes combined with HRP labelled anti-DIG Fab-fragments.

10.4. Comparison of Avidin-PtcP, Avidin-PtP and Avidin-PVA-PtP

Vimentin staining on rat liver cryostat sections was used to compare different avidin-Pt porphyrin conjugates. After an incubation with the monoclonal antibody, the slides were incubated with rabbit-anti-mouse-HRP conjugate (DAKO), followed by an incubation with BT. The biotin deposits were detected by Avidin-PtcP, Avidin-PtP and Avidin-PVA-PtP. The highest specific signals were obtained with the PVA conjugate. All slides were monitored by green and violet excitation. Violet excitation proved to be more efficient both for PtP and PtcP. Upon using the laser microscope better results were obtained with PtP labelled conjugates, due to the fact that PtP adsorbs more light of 514 nm than PtcP does.

10.5. PtP and PtcP Tyramide Based IHC and ISH With Samples Embedded in Merckoglas®

PtP and PtcP tyramides proved also to be useful in a vimentin staining of rat liver tissue sections embedded in Merckoglas®. The signal detection was improved by time-resolved microscopy.

11. Conventional IHC and ISH with PtcP-Labelled Immunoreactive Reagents 12.1. Time-Resolved ISH With c#18-, 28S- and cosmid.q2-probes on Human Metaphase Preparations Probes with various target size were used to monitor the performance of avidin-PtcP conjugates. The target size is few hundred kb (c#18-probe), 50–200 kb (28S-probe, dependent on the number of rDNA genes which ranges from ±20 for c#22 to ±100 for c#15) to ±30 kb (cosmid probe, CAD gene specific which localizes on the q2).

Single- to multilayer immunochemical approaches were tested using either biotin-, DIG-, fluorescein- or estradiol (E2) labelled probes.

| | | |
|---|---|---|
| 1 layer: | BIO-probe | detected by avidin-PtcP |
| 2 layers: | DIG-probe | detected by mouse anti-DIG biotin conjugate + avidin-PtcP |
| 3 layers: | BIO-probe | detected by avidin-PtcP + goat anti-avidin biotin conjugate + avidin-PtcP |
| | DIG-probe | detected by mouse anti-DIG + sheep anti-mouse biotin conjugate + avidin-PtcP |
| | FLU-probe | detected by rabbit anti-FITC + goat anti-rabbit biotin conjugate + avidin-PtcP |
| | E2-probe | detected by rabbit anti-E2 + goat anti-rabbit biotin conjugate + avidin-PtcP |
| 4 layers: | DIG-probe | detected by mouse anti-DIG biotin conjugate + avidin-PtcP + goat anti-avidin biotin conjugate + avidin-PtcP |

Results:

Results were monitored using either a DM microscope (continuous green excitation), CCD imaging (continuous green excitation) or with the laser microscope (time-resolved 514 nm excitation).

1 layer: Almost no visualisation of the different targets. Only the c#18-probe in combination with the CCD camera showed some results.

2 layers: Both the c#18-probe and the 28S-probe were weakly stained with the DM microscope. CCD imaging showed that an average of 7 out of 10 acocentric chromosomes were detectable. The cosmid probe was not detected with this approach.

3 layers: Results obtained from the BIO-probe were worse compared to the 2-layer approach. Similar results were found upon using fluoresceinated antibodies. For the DIG-probe different biotinylated anti-mouse IgG antibodies were tested obtained from bioSPA, Sigma, DAKO and Boehringer. The sheep anti-mouse F(ab')$_2$ biotin conjugate (Boehringer) provided the best results. More intense signals were obtained compared to the 2-layer approach. CCD imaging showed that an average of 9.5 out of 10 acocentric chromosomes were detectable. Furthermore, it was found that DIG-, FLU- or E2-labelled probes provide similar sensitivities. The cosmid probe was not done with these probes.

4 layers: All probes (except the cosmid) were easily detected using this approach and the most intensely stained signals were found with this method. The cosmid probe was not detected by the DM-microscope, however it was detected both by CCD-imaging and using the laser microscope (without camera).

11.3. mRNA Detection

HelaX1 cells were used to detect 28S rRNA molecules using the 2-layer approach and the DM microscope (continuous green or violet excitation). The 28S probe could be detected.

12. Palladium Coproporphine 12.1. Preparation of PdcP- di-NHS and Avidin-PdcP.

Preparation of PdcP-di -NHS Ester

The di-NHS ester of palladium coproporphyrin (PdcP) was prepared by dissolving 6.2 mg PdcP in 0.8 ml dry DMF.

Then 34 μl DCC (100 mg/ml in DMF), 22 μl HBTO (100 mg/ml in DMF) and 19 μl N-hydroxysuccinimide (100 mg/ml in DMF) were added. After an 16 hr incubation at RT; PdcP-2-NHS (7.1 mM in DMF) was stored at −20° C.

12.2. Preparation of Avidin-PdcP Conjugates 2.5 mg Avidin-D was labelled as a 1 mg/ml solution in 1× NHS buffer (15 μM). PdcP-2-NHS was added either to a concentration of 45 or 90 μM (3 and 6× excess) and allowed to react for 4 hrs on ice. Purification was done with standard gel filtration. Stained conjugates were obtained. In both cases part of the PdcP label was retained as a low molecular weight product, hence, had not reacted with the avidin. These conjugates were stored at −20° C. as ±0.75 mg/ml in PBSE.

Secondly, 0.5 mg avidin-D was labelled as a 1 mg/ml solution in 1× NHS buffer (15 μM). PdcP-2-NHS was added either to a concentration of 150, 525 or 750 μM (10, 35 and 50× excess) and allowed to react for 1 hr at 30° C. Purification was done with standard gel filtration. More intensely labelled avidin was obtained. Intensity of labelling increased with the excess of PdcP-2-NHS. These conjugates were stored at −20° C. as ±0.3 mg/ml in PBSE.

From all conjugates the optimal dilution on blots was determined by spotting serial dilutions of biotinylated BSA (started with 1 μl of a 0.5 μg/μl solution). After 30 min. in TNB, the nitrocellulose blots were incubated with different dilutions in TNB of the PdcP labelled avidin, using different dilutions of Avidin-PtcP A.05 as a control. After 3×5 min. washes in TNT the blots were incubated with goat anti-avidin-D alkaline phosphatase (AP) conjugate (Vector diluted 1:1500 in TNB). After 3×5 min. washes in TNT and a short rinse in bidestillated water the filters were incubated in NBT/BCIP (Rockland).

| Avidin-PdcP | 3 × excess | 1:250 ----> | 1:50 | for IHC/ISH |
|---|---|---|---|---|
| " | 6 × excess | 1:150 ----> | 1:30 | " |
| " | 10 × excess | 1:80 ----> | 1:15 | " |
| " | 35 × excess | 1:80 ----> | 1:15 | " |
| " | 50 × excess | 1:50 ----> | 1:10 | " |

12.3. Biotin Tyramide Based IHC and ISH with PdcP Labelled Avidin-D

The avidin-PdcP conjugates were tested in 2 assays with samples embedded in Vectashield®. One was the detection of 28S rRNA in Hela-cells. A double hybridization with p1-rhodamine and 28S-DIG was performed. Using the time-resolved DM microscopy in combination with the CCD-camera and continuous violet excitation both the p1 signals in the nuclei and the PdcP signals (28S rRNA) in the nucleoli and cytoplasm were observed. This shows that the reduction of (auto)fluorescence was very sufficient using the Pd copro-porphyrin as label in combination with the time-resolved DM microscope.

Secondly vimentin was detected on rat liver cryostat sections. only continuous green excitation was used. All avidin-PdcP conjugates were tested and avidin-PtcP was used as a positive control. Best results were obtained with the 3 and 50× excess conjugates, however, the other 3 conjugates also showed specific detection of vimentin in epithelial cells of the arteries, venae and bile duct. The signals were comparable to those obtained by avidin-PtcP.

We claim:

1. A process for the preparation of a metallo-porphyrin derivative having the general formula (I):

$$M\ P\text{—}(RCOOX)_n \qquad (I)$$

wherein M is palladium or platinum,

P is a porphyrin moiety,

X is a succinimide residue, a thiophenyl residue, an aryl residue or a vinyl residue which is covalently bound to the porphyrin moiety via R, wherein R is independently in each occurrence a chemical bond, or a linker group, and n is from 1 to 4, the process comprising reacting a metallo-porphyrin having the general formula (II):

$$M\ P\text{—}(RCOOH)_m \qquad (II)$$

wherein M, P and R are defined as above and m is 1–4, with a carbodiimide, 1-hydroxybenzothiazole and an active ester coupling agent which comprises a succinimide residue, a thiophenyl residue, an aryl residue or a vinyl residue, in an organic solvent, to obtain the metallo-porphyrin derivative of formula (I).

2. The process according to claim 1,
wherein R is a chemical bond, a $C_1$–$C_{20}$ alkylene group which may contain heteroatoms, an arylene group, an aralkylene group or an alkarylene group.

3. The process according to claim 1,
wherein n is from 2 to 3.

4. The process according to claim 1,
wherein the carbodiimide is dicyclohexylcarbodiimide.

5. The process according to claim 1,
wherein the active ester coupling agent is N-hydroxysuccinimide.

6. The process according to claim 1,
wherein the molar ratio of carboxylic acid groups to be activated (n) to carbodiimide to 1-hydroxybenzothiazole to active ester coupling agent is about 1:1:1:1.

7. The process according to claim 1,
wherein the organic solvent is dry dimethylformamide.

8. The process according to claim 1,
wherein the metallo-porphyrin (II) is Pd- or Pt-3,8,13,18-tetramethyl-21H,23H-porphine-2,7,12,17-tetrapropionic acid.

9. The process of claim 1,
wherein the metallo-porphyrin (II) is Pd- or Pt-meso-tetra (4-carboxyphenyl) porphine.

10. A metallo-porphyrin derivative having the general formula (I):

$$M\ P\text{—}(RCOOX)_n \qquad (I)$$

wherein M is palladium or platinum,

P is a porphyrin moiety,

X is a succinimide residue, a thiophenyl residue, an aryl residue or a vinyl residue which is covalently bound to the porphyrin moiety via R, wherein R is independently in each occurrence a chemical bond or a linker group and n is from 1 to 4.

11. The activated metallo-porphyrin derivative according to claim 10, wherein n is 2 or 3.

12. A process for the preparation of a metallo-porphyrin conjugate, comprising coupling an activated metallo-porphyrin derivative to a molecule having at least one primary amino group, wherein the metallo-porphyrin derivative has the general formula (I):

$$M\ P—(RCOOX)_n \qquad (I)$$

wherein M is palladium or platinum, P is a porphyrin moiety, X is a succinimide residue, a thiophenyl residue, an aryl residue or a vinyl residue which is covalently bound to the porphyrin moiety via R, wherein R is independently in each occurrence a chemical bond or a linker group and n is from 1 to 4, wherein at least one bond is formed between an activated carboxylic acid ester group of the activated metallo-porphyrin derivative and the at least one primary amino group.

13. The process according to claim 12, wherein the molecule having at least one primary amino group is a polymer.

14. The process according to claim 12, wherein the molecule having at least one primary amino group is a biomolecule.

15. The process according to claim 14, wherein said biomolecule is selected from the group comprising biogenic amines, hormones, vitamins, metabolites, nucleosides, nucleotides, oligonucleotides, nucleic acids, peptides, polypeptides, glycoproteins, saccharides, lipids, cellular and viral components, cells and viruses.

16. The process according to claim 14, wherein said biomolecule is selected from the group comprising tyramine, allylamine-modified nucleotides, immunoglobulins, immunoglobulin fragments and avidin.

17. A process comprising bringing a sample into contact with a conjugate obtained by the process of claim 12 and detecting the presence of said conjugate.

18. The process according to claim 17, wherein said procedure comprises a detection of the conjugate by phosphorescence.

19. The process according to claim 17, wherein said detection comprises a time-resolved measurement.

20. The process according to claim 17, wherein said procedure comprises an immunoassay.

21. The process according to claim 17, wherein said procedure comprises a nucleic acid hybridization assay.

22. The process according to claim 17, wherein said procedure comprises an in situ and/or in vitro measurement in an autofluorescing environment.

23. The process according to claim 22, wherein said procedure comprises an in situ immunohistochemical, immunocytochemical or hybridization measurement.

24. The process according to claim 23, wherein the detection is carried out by microscope.

25. The process according to claim 22, wherein the detection is carried out on an autofluorescing membrane.

26. The process according to claim 22, wherein said procedure is a FACS-analysis.

27. The process according to claim 17, wherein said procedure comprises an oxygen measurement.

28. A method as recited in claim 17, wherein said step of detecting the presence of said conjugate comprises detecting an amount of said conjugate and/or detecting localization of said conjugate.

29. A process for the preparation of a metallo-porphyrin conjugate, comprising coupling an activated metallo-porphyrin derivative to a molecule having at least one primary amino group, wherein the metallo-porphyrin derivative has the general formula (I):

$$M\ P—(RCOOX)_n \qquad (I)$$

wherein M is palladium or platinum, P is a porphyrin moiety, X is a succinimide residue, a thiophenyl residue, an aryl residue or a vinyl residue which is covalently bound to the porphyrin moiety via R, wherein R is independently in each occurrence a chemical bond, or a linker group, and n is from 1 to 4, obtained by reacting a metallo-porphyrin having the general formula (II):

$$M\ P—(RCOOH)_m \qquad (II)$$

wherein M, P and R are defined as above and m is 1–4, with a carbodiimide, 1-hydroxybenzothiazole and an active ester coupling agent which comprises a succinimide residue, a thiophenyl residue, an aryl residue or a vinyl residue, in an organic solvent, wherein at least one bond is formed between an activated carboxylic acid ester group of the activated metallo-porphyrin derivative and the at least one primary amino group.

* * * * *